(12) United States Patent
Scafetta et al.

(10) Patent No.: US 6,337,349 B2
(45) Date of Patent: *Jan. 8, 2002

(54) SOLID COMPOSITIONS SUITABLE FOR ORAL ADMINISTRATION COMPRISING AN ALKANOYL-L-CARNITINE MAGNESIUM CITRATE

(75) Inventors: Nazareno Scafetta, Pavona di Albano; Maria Ornella Tinti, Rome, both of (IT)

(73) Assignee: Sigma-Tau Industrie Farmaceutiche Riunite S.p.A., Rome (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,730
(22) PCT Filed: Mar. 19, 1998
(86) PCT No.: PCT/IT98/00058
  § 371 Date: Sep. 24, 1999
  § 102(e) Date: Sep. 24, 1999
(87) PCT Pub. No.: WO98/44918
  PCT Pub. Date: Oct. 15, 1998

(30) Foreign Application Priority Data

Apr. 8, 1997 (IT) ......................... RM97A0198

(51) Int. Cl.$^7$ .................... A61K 31/225; A61K 31/195; C07C 69/34; C07C 229/00
(52) U.S. Cl. .................. 514/547; 514/551; 514/556; 514/561; 560/196; 562/567
(58) Field of Search ................... 514/547, 551, 514/556, 561; 560/196; 562/567

(56) References Cited

U.S. PATENT DOCUMENTS

| | | | |
|---|---|---|---|
| 4,602,039 A | * | 7/1986 | Cavazza |
| 5,071,874 A | * | 12/1991 | Scholl et al. |
| 5,576,348 A | * | 11/1996 | Kuratsune et al. |

FOREIGN PATENT DOCUMENTS

| | | |
|---|---|---|
| EP | 0 402 755 | 12/1990 |
| EP | 0 434 088 | 6/1991 |
| EP | 0 628 309 | 12/1994 |
| FR | 2 529 545 | 1/1984 |
| GB | 1 153 640 | 5/1969 |

* cited by examiner

*Primary Examiner*—Gary Geist
*Assistant Examiner*—Leigh C. Maier
(74) *Attorney, Agent, or Firm*—Nixon & Vanderhye

(57) ABSTRACT

Solid and non hygroscopic salts consisting of lower alkanoyl L-carnitine magnesium citrates are disclosed which are suitable for preparing solid composition useful as dietary/nutritional supplements for human use and as fodder supplement for veterinary purposes.

11 Claims, No Drawings

SOLID COMPOSITIONS SUITABLE FOR ORAL ADMINISTRATION COMPRISING AN ALKANOYL-L-CARNITINE MAGNESIUM CITRATE

This application is a 35 U.S.C. §371 of PCT/IT98/00058, Mar. 19, 1998.

The present invention relates to stable, non-hygroscopic, pharmacologically acceptable salts of lower alkanoyl-L-carnitines which favourably lend themselves to the preparation of solid, orally administrable compositions. The present invention also relates to such compositions.

Various therapeutic uses of alkanoyl L-carnitines are already known. For instance, acetyl-L-carnitine has been used for the treatment of pathological disturbances of the CNS, particularly Alzheimer's disease and diabetic neuropathy; propionyl-L-carnitine has been used for treating peripheral vascular diseases and congestive heart failure.

It is also known that the salts of L(−)-carnitine and its alkanoyl derivatives present the same therapeutic or nutritional activities as those of the so-called inner salts and can, therefore, be used in their place, provided these salts are "pharmacologically acceptable", i.e. they do not present unwanted toxic or side effects.

In practice, then, the choice between an "inner salt" and a true L(−)-carnitine or alkanoyl-L(−)-carnitine salt will depend essentially on availability, economical and pharmacy considerations rather than on therapeutic or nutritional considerations.

The object of the present invention is to provide stable and non-hygroscopic salts of lower alkanoyl-L-carnitines which are endowed with an enhanced therapeutical and/or nutritional efficacy with respect to their inner salt counterparts.

It should, therefore, be clearly understood that the utility of the salts of the present invention is not confined to their lack of hygroscopicity and higher stability compared to the corresponding inner salts, but also resides in their enhanced therapeutic and/or nutritional value. This value is, therefore, no longer to be attributed exclusively to the "alkanoyl-carnitine" moiety of the salt.

Because of their lack of hygroscopicity these salts can be easily compounded, particularly with a view of preparing solid, orally administrable compositions.

As is well known to experts in pharmacy, the processing of hygroscopic products entails the use of controlled-humidity chambers both for storage and for the processing itself.

Moreover, the finished products must be packed in hermetically sealed blisters in order to avoid unpleasant consequences due to humidity.

All this involves extra costs both for the storage of raw materials and for their processing and packaging.

Among the populations of the industrialised countries there is an increasingly widespread use of food supplements or "nutraceuticals" both by sportsmen (amateurs or professionals) and by people in good health.

The former use L-carnitine or food supplements containing L-carnitine because it facilitates the oxidation of fatty acids and makes a larger amount of energy available to skeletal muscle, thus allowing enhanced performance and giving rise to less accumulation of lactic acid in the athletes' muscles.

People in good health use these food supplements as health foods, i.e. for the purposes of favouring a reduction in serum fat levels and normalisation of the ratio between the various cholesterol fractions in order to prevent diseases related to lipid metabolism disorders.

It has been estimated that the amount of L-carnitine and its derivatives sold for non-ethical purposes is twice that sold for ethical purposes.

The US market for food supplements or nutraceuticals amount to approximately 250 billion dollars, whereas the estimated figure for the European market is approximately 500 billion dollars (Food Labeling News, 1994, "Nutraceuticals" Market said to be a vast one, March, Vol. 2, n° 25; King Communications Group Inc., 1993, "Nutraceuticals" Foods, Drink in Global Market, Food and Drink Daily, April, Vol. 3, n° 503).

While some non-hygroscopic salts of L-carnitine are already known, there is an increasingly widespread interest in developing non-hygroscopic salts of lower alkanoyl-L-carnitines.

For instance, EP 0 150 688 (SIGMA-TAU) discloses the acid fumarate of L-carnitine and EP 0 434 088 (LONZA) discloses the use of the non-hygroscopic L(−)carnitine L(+) tartrare (2:1) (the preparation and physico-chemical characterization of which were, however, described by D. Müller and E. Strack in Hoppe Seyler's Z. Physiol. Chem 353, 618–622, April 1972) for the preparation of solid forms suitable for oral administration.

This salt presents, however, some drawbacks, such as e.g. the release, after prolonged storage, of traces of trimethylamine which give the product an unpleasant fishy odour. U.S. Pat. No. 5,071,874 discloses L-carnitine magnesium citrate but does not teach anything as regards the possibility of preparing magnesium citrates of alkanoyl-L-carnitines, nor does it suggest that these salts, if any, would be non-hygroscopic and stable to prolonged storages. It should, furthermore, be noticed that when a non-hygroscopic salt of L-carnitine is known, no conclusion can be drawn about the possibility of obtaining similar salts of alkanoyl-L-carnitines from the same salifying acid. Indeed, e.g. L-(+)-tartaric acid which gives with L-carnitine a non-hygroscopic salt, is unable to give non-hygroscopic salts with the alkanoyl-L-carnitines, such as e.g. acetyl-L-carnitine.

The aforesaid object of the present invention, i.e. to provide not only novel, pharmacologically acceptable salts of lower alkanoyl-L-carnitines which are stable and non-hygroscopic but also possess therapeutic and/or nutritional value higher than that of the corresponding inner salts, is achieved by the salts of formula (I):

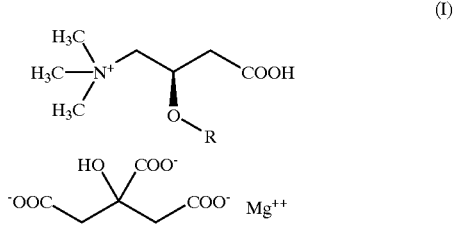

wherein R is a straight or branched lower alkanoyl having 2–5 carbon atoms.

The preferred salts are those wherein R is selected from the group comprising acetyl, propionyl, butyryl, valeryl and isovaleryl.

In the light of the aforesaid reasons, the stability and lack of hygroscopicity of the present salts was not at all foreseeable on the ground of the prior art.

Since both magnesium and carnitine are eliminated in massive amounts with the sweat and urine during prolonged, intense physical activity, the compounds of the present invention can be used to advantage as food supplements for sportsmen.

Magnesium is an important co-factor of the membrane enzymes involved in muscle contraction.

Disorders of magnesium metabolism are usually associated with a reduction in the total plasma concentration. Abnormally low blood levels of magnesium are associated with cardiovascular, neurological and skeletal muscle disorders deriving from cell contractility and excitability abnormalities.

In physiological conditions, the equilibrium constants of the reactions between $Mg^{2++}$ and ATP favour the formation of an $MgATP^{2+}$ complex which is used as a substrate by many cellular ATPases.

Magnesium also affects the properties of various ion channels, many of which are situated in various excitable cells, and thus performs a regulatory function with regard to the influx of other ions such as sodium, calcium and potassium.

Magnesium exerts a protective action on cardiac function. The involvement of magnesium in influencing cardiovascular function has recently received considerable attention, both as a therapeutic agent to minimise disorders of an electrophysiological nature and as an aetiological factor in diseases such as myocardial decompensation and hypertension. Epidemiological studies have revealed that there is a distinct correlation between the incidence of cardiac ischaemia and the calcium:magnesium ratio in the diet and drinking water. Hypomagnesaemia gives rise to muscle cramps and to increased activity of the autonomic system.

The following non-limiting example shows the preparation of a non-hygroscopic salt according to the present invention.

EXAMPLE

Preparation of Acetyl-L-carnitine Magnesium Citrate (ST 1304)

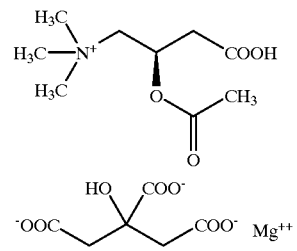

Acetyl-L-carnitine inner salt (1 mole), citric acid (1 mole) and $Mg(OH)_2$ (1 mole) were suspended in $H_2O$ and kept under stirring for about 30 minutes.

The resulting solution was then concentrated under vacuum. The residue was taken up with acetone and the resulting mixture kept under stirring and then filtered.

A solid, non-hygroscopic product was obtained.

Yield: 95%.

| Elementary analysis for $C_{15}H_{23}NO_{11}Mg$ | | | | |
|---|---|---|---|---|
| | C % | H % | N % | Mg |
| Calculated (with 4.1% $H_2O$): | 41.37 | 5.78 | 3.22 | 5.58 |
| Found: | 40.69 | 5.47 | 2.50 | 5.6 |

$[\alpha]_D^{25}=-12.7$ (c=1%, $H_2O$)

DSC (dec.): 160° C.–170° C.

NMR $D_2O$ δ5.6(1H,m,C$\underline{H}$OH); 3.8(1H,dd,N$^+$C$\underline{H}$H); 3.4 (1H,dd,N$^+$—CH$\underline{H}$); 3.2(9H,s,(CH$_3$)$_3$N$^+$); 3.4(1H,m,C$\underline{H}$HCOOH); 2.8–2.75(2H,d,C$\underline{H}_2$COOH citrico); 2.65–2.60 (2H,d,C$\underline{H}_2$COOH citrico) 2.7–2.5(1H,m,CH$\underline{H}$—COOH); 2.2(3H,s,COCH$_3$).

| HPLC: | |
|---|---|
| Colum: | Inertsil-ODS-3 (5 μm) 250 × 4.6 mm |
| Eluant: | NaClO$_4$ 0.15 M + NaH$_2$PO$_4$ 0.05 M/1 H$_2$O |
| pH: | 2 with H$_3$PO$_4$ |
| Flow-rate: | 0.75 mL/min |
| Citric acid: | R$_1$ = 9.53 min |
| Acetyl-L-carnitine: | R$_1$ = 19.47 min |

The present invention also relates to compositions comprising as active principle(s) at least one of the aforesaid non-hygroscopic pharmacologically acceptable salts and, optionally, one or more pharmacologically acceptable excipients and active ingredients which are well-known to the experts in pharmacy and food technology.

Particularly preferred are the solid, orally administrable compositions such as tablets, chewable tablets and capsules, which comprise a salt of alkanoyl-L-carnitine of formula (I) in an amount corresponding to 50–2,000, preferably 100–1,000, mg alkanoyl-L-carnitine inner salt.

For instance, a composition for preparing tablets is the following:

| | |
|---|---|
| Non-hygroscopic alkanoyl-L-carnitine salt of formula (I) | 500 mg |
| Starch | 20 mg |
| Talc | 10 mg |
| Calcium stearate | 1 mg |
| | 531 mg |

A composition suitable for preparing capsules is the following:

| | |
|---|---|
| Non-hygroscopic alkanoyl-L-carnitine salt of formula (I) | 500 mg |
| Starch | 20 mg |
| Lactose | 50 mg |
| Talc | 5 mg |
| Calcium stearate | 2 mg |
| | 577 mg |

The compositions of the present invention may be used as dietary/nutritional supplements for human use or as fodder supplement for veterinary purposes.

Through the synergic action exerted by the component moieties of the present salts, the following results are achieved:

enhanced enzymatic activity bound to the energy metabolism;

improved endurance and adaptation to programs of strenous exercise with achievement of higher performances and shorter rest periods;

strengthening of the functional capacity of the cardiovascular system; and
less tendency to develop muscular cramps.

What is claimed is:

1. A salt of alkanoyl-L-carnitine of formula (I)

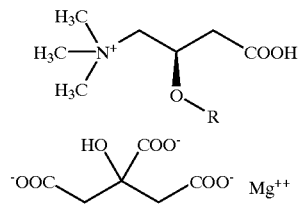

wherein R is a straight or branched lower alkanoyl having 2–5 carbon atoms.

2. The salt of claim 1, wherein R is selected from the group comprising acetyl, propionyl, butyryl, valeryl and isovaleryl.

3. Acetyl-L-carnitine magnesium citrate.

4. Propionyl-L-carnitine magnesium citrate.

5. A composition comprising as active ingredient a salt of claim 1.

6. The composition of claim 5, further comprising one or more substances selected from pharmacologically acceptable excipients and active ingredients.

7. The composition of claim 5, in the form of tablets, chewable tablets, capsules, granulates or powders.

8. The composition of claim 5, in unit dosage form comprising as active ingredient a salt of alkanoyl-L-carnitine of formula (I), in an amount corresponding to 50–2,000 mg of alkanoyl-L-carnitine inner salt.

9. The composition of claim 8, wherein the amount of the salt of alkanoyl-L-carnitine of formula (I) corresponds to 100–1,000 mg of alkanoyl-L-carnitine inner salt.

10. A dietary or nutritional supplement for human use comprising the salt of claim 1.

11. A dietary of nutritional animal fodder supplement comprising the salt of claim 1.

* * * * *